US005686263A

United States Patent [19]
Wurm

[11] Patent Number: 5,686,263
[45] Date of Patent: Nov. 11, 1997

[54] METHOD FOR ENHANCING GENE EXPRESSION

[75] Inventor: Florian M. Wurm, Redwood City, Calif.

[73] Assignee: Genentech, Inc., South San Francisco, Calif.

[21] Appl. No.: 157,007

[22] PCT Filed: May 29, 1992

[86] PCT No.: PCT/US92/04469

§ 371 Date: Jan. 28, 1994

§ 102(e) Date: Jan. 28, 1994

[87] PCT Pub. No.: WO92/21763

PCT Pub. Date: Dec. 10, 1992

Related U.S. Application Data

[63] Continuation-in-part of Ser. No. 708,155, May 31, 1991, abandoned.

[51] Int. Cl.$^6$ .............................. C12P 21/02; C12N 15/64
[52] U.S. Cl. ................................ 435/69.1; 435/172.3
[58] Field of Search ........................ 435/172.3, 240.2, 435/320.1, 69.1

[56] References Cited

U.S. PATENT DOCUMENTS 4,396,601 8/1983 Salser et al. ........................ 424/94.5

FOREIGN PATENT DOCUMENTS

| 310586 | 4/1989 | European Pat. Off. | C12N 15/00 |
|---|---|---|---|
| WO 90/14092 | 1/1990 | WIPO | A61K 31/70 |
| WO 90/05787 | 5/1990 | WIPO | C12P 21/00 |
| WO 90/12880 | 11/1990 | WIPO | C12N 15/86 |
| WO 91/01140 | 2/1991 | WIPO | A61K 37/00 |
| WO 91/06666 | 5/1991 | WIPO | C12P 21/06 |
| WO 91/06667 | 5/1991 | WIPO | C12P 21/06 |
| WO 92/01800 | 2/1992 | WIPO | C12N 15/84 |
| WO 92/10577 | 6/1992 | WIPO | C12N 15/81 |

OTHER PUBLICATIONS

Lacy et al., *Cell*, vol. 34, 1983, pp. 343–358.
Jaenisch et al., *Bioch. Biophys. Acta*, vol. 782, 1984, pp. 1–9.
Kuff et al., "Homology between an endogenous viral LTR and sequences inserted in an activated cellular oncogene", *Nature*, 302: 547–548 (1983).
Collen, D. et al., "Biological Properties of Human Tissue-Type Plasminogen Activator Obtained by Expression of Recombinant DNA in Mammalian Cells", *J.Pharm.Exp.* 231(1):146–152 (1984).
Ymer et al., "Constitutive synthesis of interleukin-3 by leukaemia cell line WEHI-3B is due to retroviral insertion near the gene", *Nature*, 317: 255–258 (1985).
Stocking et al., "Identification of Genes Involved in Growth Autonomy of Hematopoietic Cells by Analysis of Factor-Independent Mutants", *Cell*, 53: 869–879 (1988).
Blatt et al., "DNA rearrangement of a homeobox gene in myeloid leukaemic cells." *EMBO J.*, 7(13): 4283–4290 (1988).

Shen–Ong and Cole, "Amplification of A Specific Set of Intracisternal A–Particle Genes in a Mouse Plasmacytoma", *J. Virol.*, 49(1): 171–177 (1984).
Liskay et al., "Homologous Recombination between Repeated Chromosomal Sequences in Mouse Cells", *Cold Spring Harbor Symposia Quant. Biol.*, 49: 183–189(1984).
Murnane, J.P. & Yezzi, M. J., "Association of High Rate of Recombination with Amplification of Dominant Selectable Gene in Human Cells" *Somatic Cell and Molecular Genetics*, 14(3): 273–286 (1988).
Patzer, E.J., "Cell culture derived HBsAG is highly immunogenic and protects chimpanzees from infection with hepatitis B virus", *BioTechnology* 4:630–636 (1986).
Egrie, J.C., "Characterization of recombinant monkey and human erythropoietin", *Prog.Clin.Biol.* 191:339–350 (1985).
Lau et al., "Amplification and Expression of Human α–Globin Genes in Chinese Hamster Ovary Cells", *Mol. and Cell. Biology*, 4(8): 1469–1475 (1984).
Wurm et al., "Host Cell Derived Retroviral Sequences Enhance Transfection and Expression Efficiency in CHO Cells", *Animal Cell Technology: Developments, Processes & Products*, Spier et al. eds. Butterworths, pp. 35–41 (1990).
Amariglio & Rechavi, "Insertional Mutagenesis by Transposable Elements in the Mammalian Genome", *Environmental and Molecular Mutagenesis*, 21:212–218 (1993).
Anderson et al., "Endogenous Origin of Defective Retroviruslike Particles from a Recombinant Chinese Hamster Ovary Cell Line", *Virology*, 181: 305–311 (1991).
Baltimore, David, "Retroviruses and Retrotransposons: The Role of Reverse Transcription in Shaping the Eukaryotic Genome", *Cell* 40:481–482 (1985).
Windle et al., "A central role for chromosome breakage in gene amplification, deletion formation, and amplicon integration", *Genes and Development* 5:150–174 (1991).
Lueders et al.,"Characterization of amplified intracisternal A–particle elements encoding integrase", *Nucleic Acids Res.*, 17(22): 9267–9277 (1989).
Ferguson et al., "Chromosomal localization of genes by scanning electron microscopy using in situ hybridization with biotinylated probes: Y chromosome repetitive sequences", *Histochemical Journal*,18: 266–270 (1986).
Lopes, T. et al., "High–copy–number integration into the ribosomal DNA of *Saccharomyces cerevisiae*: a new vector for high–level expression", *Gene*, 79: 199–206 (1989).

(List continued on next page.)

Primary Examiner—Mindy Fleisher
Assistant Examiner—James Ketter
Attorney, Agent, or Firm—Richard B. Love

[57] ABSTRACT

Methods are provided for the identification and use of endogenous nucleic acid sequences for homologous recombination and targeted integration of heterologous nucleic acid sequences. These methods are useful for introduction of nucleic acid into cells or tissue for gene therapy, or for the preparation of transgenic animals. Methods are also provided for enhancing the yield of genes of interest from recombinant cell culture lines.

14 Claims, 6 Drawing Sheets

OTHER PUBLICATIONS

Thomas et al., "High Frequency Targeting of Genes to Specific Sites in the Mammalian Genome", *Cell* 44:419–428, (1986).

Zheng et al., "Gene targeting in normal and amplified cell lines", *Nature* 344:170–173 (1990).

Kasid et al., "Effect of Antisense c–raf–1 on Tumorigenicity and Radiation Sensitivity of a Human Squamous Carcinoma", *Science* 243:1354–1356 (1989).

Khokha et al., "Antisense RNA–Induced Reduction in Murine TIMP Levels Confers Oncogenicity on Swiss 3T3 Cells", *Science* 243:947–950 (1989).

Izant et al., "Constitutive and Conditional Suppression of Exogenous and Endogenous Genes by Anti–Sense RNA", *Science* 229:345–352 (1985).

von Ruden et al., "Inhibition of Human T–Cell Leukemia Virus Type I Replication in Primary Human T Cells That that Express Antisense RNA", *J. Virol.* 63(2):677–682 (1989).

Chang et al., "Inhibition of Rous Sarcoma Virus Replication by Antisense RNA", *J. Virol.* 61(3):921–924 (1987).

Kerr et al., "Excess antisense RNA from inectious recombinant SV40 fails to inhibit expression of a transfected, interferon–inducible gene", *Eur. J. Biochem.* 175:65–73 (1988).

Donahue, P. R. et al., "Strong Sequence Conservation among Horizontally Transmissible, Minimally Pathogenic Feline Leukemia Viruses", *J. Virol.* 62(3): 722–731 (1988).

Lieber, M.M., "Mammalian Cells in Culture Frequently Release Type C Viruses", *Science* 182:56–58 (1973).

Lubiniecki, "Endogenous retroviruses of continuous cell substrates", *Develp. biol. Standards* 70:187–191 (1989).

Lubiniecki et al., "Cell bank characterization for recombinant DNA mammalian cell lines", *Develp. biol. Standards* 60:141–146 (1985).

Manley, K.F. et al., "Characterization of Virus–like Particles Released from the Hamster Cell Line CHO–K1 After Treatment with 5–Bromodeoxyuridine", *J. gen. Virol.* 39:505–517 (1978).

Tihon & Green, "Cyclic AMP–amplified Replication of RNA Tumour Virus–like Particles in Chinese Hamster Ovary Cells", *Nat. New Biol.* 244:227–231 (1973).

Hojman, F.R., "Biological and Molecular Characterization of an Endogenous Retrovirus Present in CHO/HBs–A Chinese Hamster Cell Line", *Develop. biol. Standard,* 70:195–202 (1990).

Anderson et al., "Presence and Transcription of Intracisternal A–Particle–Related Sequences in CHO Cells", *Journal of Virology* 64(5):2021–2032 (1990).

Jasin et al., "High Frequency of Homologous Recombination in Mammalian Cells between Endogenous and Introduced SV40 Genomes", *Cell* 43:695–703 (1985)(Part 2).

Finn et al., "Homologous Plasmid Recombination is Elevated in Immortally Transformed Cells", *Molecular and Cellular Bioloqy* 9(9):4009–4017 (1989).

Rauth et al,, "Transfection and homologous recombination involving single–stranded DNA substrates in mammalian cells and nuclear extracts", *Proc. Natl. Acad. Sci. USA* 83:5587–5591 (1986).

Smithies et al., "Insertion of DNA sequences into the human chromosomal β–globin locus by homologous recombination" *Nature* 317:230–234 (1985).

Jasin et al., "Gene targeting at the human CD4 locus by epitope addition", *Genes & Development* 4:157–166 (1990).

Korenberg et al., "Human Genome Organization: Alu, Lines, and the Molecular Structure of Metaphase Chromosome Bands" *Cell* 53:391–400 (1988).

Gasser et al., "A glimpse at chromosomal order", *Trends in Genetics* 3:16–22 (1987).

Gasser et al., "The organisation of chromatin loops: characterization of a scaffold attachment site" *EMBO J.* 5(3):511–518 (1986).

Colbere–Garapin et al., "DNA Transfection into Mammalian Cells, Selective Markers and Gene Cointegration" *Develop. biol. Standard* 70:85–89 (1989).

Ma et al., "Organization and Genesis of Dihydrofolate Reductase Amplicons in the Genome of a Methotrexate–Resistant Chinese Hamster Ovary Cell Line", *Mol. and Cell. Biol.* 8(6):2316–2327 (1988).

Wahl, et al., "Effect of chromosomal position on amplification of transfected genes in animal cells", *Nature* 307:516–520 (1984).

Christman et al., "Amplification of expression of hepatitis B surface antigen in 3T3 cells cotransfected with a dominant–acting gene and cloned viral DNA", *Proc. Natl. Acad. Sci. USA* 79:1815–1819 (1982).

Kaufman et al., "Coamplification and Coexpression of Human Tissue–Type Plasminogen Activator and Murine Dihydrofolate Reductase Sequences in Chinese Hamster Ovary Cells", *Mol. and Cell. Biol.* 5(7):1750–1759 (1985).

Robins et al., "Transforming DNA Integrates into the Host Chromosome", *Cell* 23:29–39 (1981).

Kaufman et al., "Amplification and Expression of Sequences Cotransfected with a Modular Dihydrofolate Reductase Complementary DNA Gene", *J. Mol. Biol.* 159:601–621 (1982).

Mansour et al., "Disruption of the proto–oncogene int–2 in mouse embryo–derived stem cells: a general strategy for targeting mutations to non–selectable genes", *Nature* 336:348–352 (1988).

Weidle et al., "Amplified expression constructs for human tissue–type plasminogen activator in Chinese hamster ovary cells: instability in the absence of selective pressure", *Gene* 66:193–203 (1988).

Thomas et al., "Site–Directed Mutagenesis by Gene Targeting in Mouse Embryo–Derived Stem Cells", *Cell* 51:503–512 (1987).

Song et al., "Accurate modification of a chromosomal plasmid by homologous recombination in human cells", *Proc. Natl. Acad. Sci. USA* 84:6820–6824 (1987).

Barsoum "Laboratory Methods–Introduction of Stable High–Copy–Number DNA into Chinese Hamster Ovary Cells by Electroporation", *DNA and Cell Biology* 9(4):293–300 (1990).

Rubnitz et al. "The Minimum Amount of Homology Required for Homologous Recombination in Mammalian Cells", *Mol. and Cell. Biol.* 4(11):2253–2258 (1984).

Kim et al., "Recombinant fragment assay for gene targeting based on the polymerase chain reaction" *Nucl. Acids Res.* 16:8887–8903 (1988).

Pinkel et al., "Fluorescence in situ hybridization with human chromosome–specific libraries: Detection of trisomy 21 and translocations of chromosome 4", *Proc. Natl. Acad. Sci.,* 85:9138–9142 (1988).

Wichman et al., "Transposable elements and the evolution of genome organization in mammals", *Genetica,* 86: 287–293 (1992).

Deininger, Prescott, "Sines: Short Interspersed Repeated DNA Elements in Higher Eucaryotes", *Mobile DNA*, Berg & Howe, eds., Chap. 27, pp. 619–636 (1989).

Singer & Skowronski, "Making sense out of Lines: long interspersed repeat sequences in mammalian genomes", *TIBS*, 119–124 (Mar. 1985).

Miles & Meuth, "G-repeats: a novel hamster sine family", *Nucleic Acids Research*, 17(18): 7221–7228 (1989).

Weiner et al.,"Nonviral retroposons: genes, pseudogenes, and transposable elements generated by the reverse flow of genetic information", *Ann. Rev. Biochem.*, 55:631–661 (1986).

Shen-Ong & Cole, "Differing Populations of Intracisternal A-Particle Genes in Myeloma Tumors and Mouse Subspecies", *J. Virol.*,42(2): 411–421 (1982).

Schmid & Maraia, "Transcriptional regulation and transpositional selection of active Sine sequences", *Current Opinion in Genetics and Develop.*, 2:874–882 (1992).

Kimmel, Alan R., "Selection of clones from libraries: Overview" *Methods in Enzymology* 152:393–399 (1987).

Kuff et al., "Intracisternal A-Particle Genes in Mus musculus: a conserved family of retrovirus-like elements" *Molecular & Cellular Biology* 1(3):216–227 (1981).

Stearns et al., "Manipulating yeast genome using plasmid vectors" *Methods in Enzymology* 185:280–297 (1990).

Wurm, F., "Retrotargeting: Use of Defective Retroviral DNA Fragments to Improve Recombinant Protein Production in Mammalian Cells" *Animal Cell Technology; Products of Today, Prospects for Tomorrow* (12th Mtg. Eur. Society for Animal Cell Tech., May 1993), Spier et al., Butterworth Heinmann pp. 24–29 (1994).

METHOD FOR ENHANCING GENE EXPRESSION

This is a continuation-in-part of application Ser. No. 07/708,155, filed 31 May 1991, now abandoned.

BACKGROUND OF THE INVENTION

This invention relates to recombinant cell culture lines and methods, particularly to the identification and use therein of endogenous nucleic acid sequences for homologous recombination and targeted integration of heterologous nucleic acid sequences. This invention further relates to the therapeutic introduction of nucleic acid sequences into cells or tissue, particularly through targeted integration using homologous recombination; this introduction is useful for gene therapy, or for the creation of transgenic animals.

Gene therapy is the introduction of nucleic acid into a cell or tissue either in vivo or ex vivo. In some instances, the nucleic acid is intended to replace (or act in place of) a functionally deficient endogenous gene, to confer on the host the ability to produce a therapeutic polypeptide, to cause repression of an undesirable gene product, or to stimulate an immune response. Methods are known for introducing nucleic acid into cells in vitro or into such cells or tissues ex vivo, including the insertion of naked DNA or RNA such as by injection into tissue, the use of techniques such as electroporation, the provision of nucleic acid in liposomes or other carrier, the use of a vector such as a virus, retrovirus, phage, plasmid etc., and the reintroduction into a tissue of a cell modified ex vivo to transcribe and express heterologous nucleic acid.

Other researchers have made transgenic animals which transcribe and express heterologous nucleic acid. Such animals have been produced by transfecting germ cells, somatic cells, or embryos with heterologous nucleic acid, suitably implanting the transfected cells and allowing the cells to mature into or stably integrate into adult animals containing the heterologous DNA. A reproducible percentage of such animals transcribe and express the heterologous nucleic acid as protein which can be identified in tissues including blood or serum. Methods for making transgenic animals are described in U.S. Pat. No. 4,396,601.

Recombination involves the opening and cross-wise rejoining of nucleic acid strands within homologous sequences. Intramolecular recombination (recombination between homologous sequences present on a single nucleic acid molecule) has been described in the literature. For example, it has been shown that intramolecular recombination occurs between tandemly arranged, identical, homologous and partially homologous DNA sequences.

Intermolecular recombination is the term used to describe recombination between two different nucleic acid molecules, for example, between two homologous chromosomes during meiosis, or between different viral genomes present in the same infected cell. Intermolecular recombination has been shown in a number of different animal viruses, and this process has been used for the generation of vectors for the cloning and expression of heterologous DNA sequences. Typically, the virus is used as an infectious cloning vector.

It has been shown that, following their introduction into mammalian cells, certain DNA molecules do recombine with each other through shared homologous regions. See, for example, Thomas et al., Cell 44:419–428 (1986), and Zheng et al., Nature 344:170 (1990). Such integration of heterologous DNA into mammalian cells in culture has numerous potential applications, including research, vaccine development, and gene therapy.

Recombination using antisense technology has previously been used to inhibit expression of specific gene products in mammalian cell lines (Kasid et al., Science 243:1354–1356 [1989]; Khoka et al., Science 243:947–950 [1989]; Izant et al., Science 229:345–352 [1985]) including some retroviruses; (von Ruden et al., J. Virol. 63:677–682 [1989]; Chang et al., J. Virol. 61:921–924 [1987]), but not all attempts have been successful (Kerr et al., Eur. J. Biochem. 175:65–73 [1988]). The secondary structure of the endogenous target RNA may influence susceptibility to antisense inhibition. Antisense inhibition is currently believed to require an excess of antisense RNA relative to coding mRNA in order to be effective.

Various methods are currently used for the introduction into and amplification of foreign (heterologous) nucleic acid into cultured cells for research purposes as well as for the purpose of overproduction of proteins of interest for pharmaceutical applications. While a lot of knowledge has been accumulated over the years with respect to optimized expression plasmid vectors and their individual regulatory components, little is known about the mechanisms, limitations and obstacles for successful integration of the donor DNA into the chromosomal DNA of the recipient host cells. In eukaryotic cell culture, despite efforts to optimize expression vectors, typically only a rather small percentage of clonal cell lines established following transfection with heterologous donor DNA actually express the gene of interest. Of those cell lines which do express the gene of interest, often only a small percentage express the protein of interest at satisfying levels.

It is possible that factors inherent in the host cell and its genome have an effect on expression level of the protein of interest. It is possible that one of the variables affecting expression-levels is the site of integration of the donor DNA into the host chromosomal DNA. For example, integration of the donor DNA may occur in areas which are not transcriptionally active, or in non-coding areas of the host DNA (DNA which is represented by highly and moderately repetitive sequences which seem not to code for any product and possibly have only structural functions). It is possible that integration of donor DNA into these regions does not result in adequate levels of the regulatory nuclear proteins which are necessary for high levels of transcription. Thus, integration of plasmid or donor DNA into these regions may result in absent or low expression of the gene of interest.

Researchers in the field have contemplated the question of how to determine that the incoming DNA be integrated into sites within chromosomes where transcription rates are high. For that purpose, researchers have used specific selection procedures and recombination of nucleic acid sequences which are homologous to sequences in the host cell's genomic DNA to achieve "targeted integration" rather than random integrations, see e.g. Zheng et al., supra. Only partial success have been reported; generally targeted integration was seen only in about 1 in 1000 events, with the majority of recombinant cell lines established having the donor DNA integrated at random sites.

It is known that eukaryotic cells contain endogenous sequences which are transcribed at high rates and are present in relatively high copy number, generally 2–20 times, some more than 20, and transcripts of some sequences are found with hundreds of copies. Some of these sequences are dispersed throughout the host genome, on more than one chromosome.

Cultured Chinese hamster ovary (CHO) cells are frequently used in research and in the production of proteins of interest. Retrovirus-like particles are observed in all CHO cells when thin-sections of cells are viewed by transmission electron microscopy. Two types of particles are consistently observed: Intracytoplasmic A-type particles frequently associated with centrioles, and budding C-type particles {Donahue, P. R, et al., *J. Virol.* 62:722–731 [1988]; Lieber, M. M. *Science* 182:56–58 [1973]; Lubiniecki, *Develp. Biol. Standards* 70:187–191 [1989]; Lubiniecki et al., *Develp. Biol. Sta* 60:141–146 [1985]; Manley, K. F. *J. Gen. Virol.* 39:505–517 [1978]; Tihon, C., *Nat. New Biol.* 244:227–231 [1973]}. Infection or transmission to other cells has never been detected {ibid., and Hojman, F. R., *Develop. Biol.* 70:195–202 [1990]}. Despite their apparently non-infectious nature, the origin of the observed retrovirus-like particles is of interest since recombinant CHO cells are used as substrates for the production of biopharmaceuticals intended for human use {Colien, D., *J. Pharm. Exp.* 231:146–152 [1984]; Patzer, E. J., *Bio Technology* 4:630–636–636 [1986]; Egrie, J. C., *Prog. Clin. Bio.* 191:339–350 [1985]}. To the extent mat reverse transcriptase activity, indicative of potential biological activity, is shown to be associated with retrovirus-like particles in recombinant cell lines, concern is heightened regarding potential transmission of virus to recipients of biopharmaceutical products.

It has been found that families of such sequences are present in these cells at high copy numbers: IAP like sequences are present at about 500 to 1000 copies per genome and C-type sequences at about 100–300 copies per genome (Anderson et al., *J. Virology* 64:2021–203 (1990); Wurm et al., *Advances in Animal Cell Biology and Technology for Bioprocesses* p. 71990 (Spier et al., eds. Butterworths, (1990)); Anderson et al., *Virology* 181:305 (1991)).

It is an object of is invention to provide methods for the increased transcription of genes of interest in eukaryotic cell culture. It is a further object of this invention to provide methods for the introduction of nucleic acid in cells or tissue of an animal, in vitro, in vivo or ex vivo.

It is another object of this invention to provide methods for targeted integration of heterologous nucleic acid into a host eukaryotic cell, which methods result in enhanced yields of a gene of interest.

It is a further object of this invention to utilize nucleic acid sequences which are endogenous in a host cell to enhance expression of genes of interest.

SUMMARY OF THE INVENTION

The objects of this invention are accomplished through the provision of methods for obtaining eukaryotic cells having increased expression of a heterologous gene comprising: 1) obtaining a eukaryotic cell having a first endogenous nucleic acid sequence; and introducing into said cell a second nucleic acid sequence homologous to said endogenous sequence and a third nucleic acid sequence which encodes a heterologous gene.

In some aspects of this invention, the second and third nucleic acid sequences are introduced into the host cell through a plasmid vector. It is preferred that the third nucleic acid sequence which encodes the heterologous gene be under the control of transcription control sequences, while the second nucleic acid sequence need not.

In certain embodiments, the endogenous sequence is a retrovirus-like sequence, and in some embodiments this retrovirus-like sequence is unable to form infectious virus. It is desirable to use retrovirus-like sequences which are defective in their native form, however they may also be rendered non-infectious through recombinant manipulations.

In certain preferred embodiments, the host cell is a CHO cell and the endogenous retrovirus-like nucleic acid sequence is selected from the group consisting of nucleic acid encoding intracytoplasmic A-type, B-type, or C-type particles.

In some embodiments, the nucleic acid encoding the heterologous gene is introduced into the host cell in greater copy number than is the second nucleic acid sequence.

For obtaining greatly enhanced yields, it is preferred that the first endogenous nucleic acid sequence be present in the genome of the host cell in at least two copies, preferably 2–20, more preferably 20–100, and most preferably more than 100 copies. For obtaining greatly enhanced yields, it is also preferred that the first endogenous nucleic acid sequence be dispersed through the genome of the cell, preferably on at least two different chromosomes.

It is anticipated that the nucleic acid be introduced into the host cell in double-stranded form or as a single strand.

In other aspects of this invention, methods are provided identifying suitable endogenous candidate nucleic acid sequences for use in the methods previously described. These identification methods include screening for a nucleic acid sequence which is endogenous in a eukaryotic cell and which is transcribed in at least two copies, and preferably is dispersed within the genome of the host cell. It is presently preferred that the copies be present on different chromosomes, or on different loci of the same chromosome, or on the same chromosome but separated from each other by at least about 100,000 base pairs.

It is also preferred that these endogenous sequences be present in transcriptionally active regions of the host cell genome. Polynucleotide probes can be made for determining the level of transcription of the endogenous DNA in cells using common methods and without undue experimentation.

In certain embodiments, the use of endogenous sequences are preferred which are amplified to quite high copy numbers and also are distributed almost evenly throughout the genome. While the precise mechanisms are not precisely known at this time, the inventor suggests that, using such selection criteria, introduced DNA entering the cell would have to "travel" only short distances in order to reach their targets, and therefore integration into or close to these endogenous sequences within the host cell genome would be favored and result in the high transcription rates described herein.

Particularly preferred endogenous sequences useful in the practice of this invention include transposon sequences, sequences encoding members of the immunoglobulin gone superfamily, globin family sequences, retroviral sequences, retrovirus-like sequences, histocompatibility sequences, and amplicon sequences.

BRIEF DESCRIPTION OF THE DRAWINGS

FIG. 1-2: shows a map of a 6.6 kb fragment representing about 70% of a complete C-type particle retrovirus genome. About 450 basepairs upstream of the 5' LTR to a Sal 1 site 2 kb upstream of the 3' LTR was used. Also, an internal 1.7 kb PstI-PstI fragment including the 5' LTR was used in transfections.

FIG. 2 shows the number of selected colonies in co-transfections containing and lacking IAP-retroviral sequences.

FIG. 4-1: Expression levels of randomly chosen cell clones upon selection in GHT minus medium FIG. 4-2: Cell clones expressing greater than 500 ng/ml of CD4IgG FIG. 4-3: Expression levels exceeding 1000 ng/ml in randomly chosen cell clones upon co-transfections with DHFR-plasmid containing or lacking a 2.9 kb IAP-retrovirus like sequence in two orientations.

FIG. 4-4: Expression ranges for CD4IgG of randomly chosen cell clones following co-transfection with DHFR expression plasmids containing and lacking a 2.9 kb IAP retrovirus-like DNA from CHO cells and an expression vector for CD4IgG.

DETAILED DESCRIPTION

Figure 1:
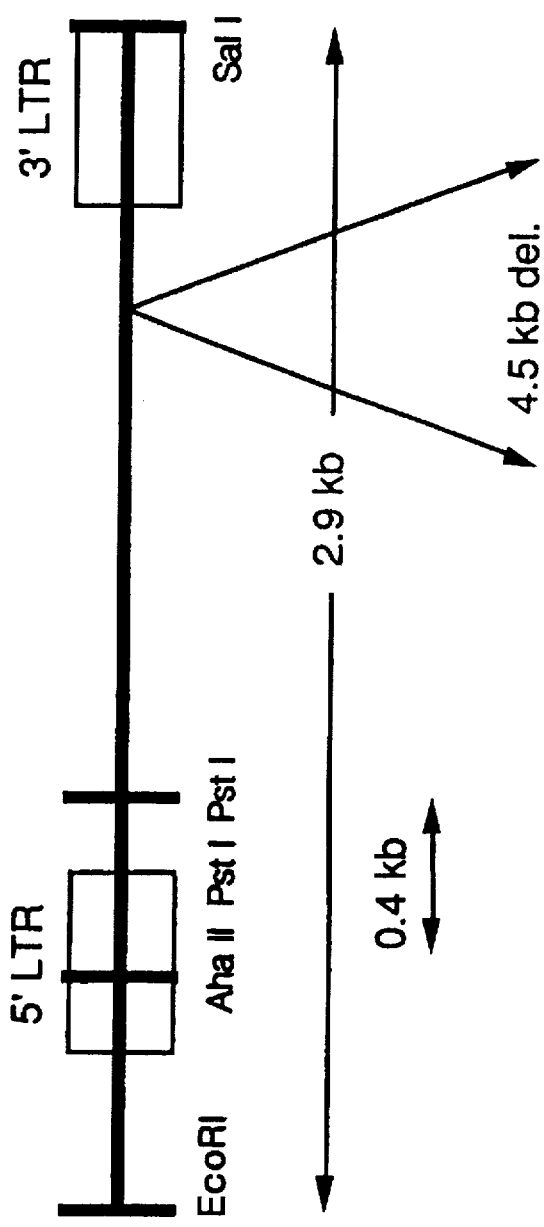
FIG. 1-1: shows a restriction map of an IAP particle sequence which has been isolated from the CHO-genome as a genomic DNA fragment (EcoRI-Sal I) of 2.9 kb of length. The figure also shows a 0.4 kb subfragment from this DNA. The 0.4 kb fragment (Aha II-Pst I) represents part of the 5' LTR sequence of the larger 2.9 kb "full length" IAP-like DNA. The 2.9 kb "full length" IAP DNA spans from an EcoRI site about 400 basepairs upstream of the 5' LTR to a Sal I site inside of the 3' LTR. This retrovirus-like DNA has an internal 4.5 kb deletion which excises a major part of the "virus genome".

C-type retrovirus-like particles are budding particles with retrovirus-like morphology and immunological characteristics, described generally in the literature cited above. Intracytoplasmic A-type particles frequently associated with centrioles are specifically excluded from this definition. C-type retrovirus nucleic acid sequences are defined herein as sequences encoding such particles, allowing for multiple interruptions of potential coding sequences.

Homology with respect to any endogenous sequence is defined herein as the percentage of residues in the candidate sequence that are identical with the residues in the endogenous sequence as published in the literature or identified by the researcher, after aligning the sequences and introducing gaps, if necessary, to achieve the maximum percent homology. Where the candidate sequence is homologous to an endogenous sequence, preferably but not necessarily it has at least ~60% homology to the endogenous sequence.

An "exogenous" element is defined herein to mean foreign to the cell, or homologous to the cell but in a position within the host cell in which the element is ordinarily not found. An "endogenous" element is defined herein to mean native to the cell. An "endogenous nucleic acid sequence" is defined to mean a nucleic acid sequence which is endogenous to the cell.

Nucleic acid compositions which are complementary (antisense) to endogenous sequences are encompassed herewith. It is intended that single-stranded and double-stranded DNA be utilized in the practice of this invention. Within the scope of this invention is this complementary DNA, as well as complementary RNA transcripts, and fragments of such complementary DNA and RNA sequences which retain hybridization specificity to the endogenous sequence utilized.

Signal sequence fusions are employed in order to more expeditiously direct the secretion of the gene product of interest. A heterologous signal may replace the native particle signal, and when the resulting fusion is recognized, i.e. processed and cleaved by the host cell, the retrovirus-like particle is secreted. Signals are selected based on the intended host cell, and may include-bacterial, yeast, mammalian and viral sequences. The native signal or the herpes gD glycoprotein signal is suitable for use in mammalian expression systems.

Nucleic acid encoding the endogenous sequences or the heterologous genes of this invention is synthesized by in vitro methods or is obtained readily from cDNA libraries. The means for synthetic creation of the DNA, either by hand or with an automated apparatus, are generally known to one of ordinary skill in the art, particularly in light of the teachings contained herein. As examples of the current state of the art relating to polynucleotide synthesis, one is directed to Maniatis et al., Molecular Cloning-A Laboratory Manual, Cold Spring Harbor Laboratory (1984), and Horvath et al., An Automated DNA Synthesizer Employing Deoxynucleoside 3'-Phosphoramidites, Methods in Enzymology 154:313–326, 1987.

It is anticipated that desirable endogenous nucleic acid sequences will be identified for each host cell. One method for such an identification involves the analysis of gene transcripts encoded by the host cell genome, particularly looking for sequences which are present in at least two copies, preferably 2–20, more preferably 20–100, and even more preferably greater than 100 copies. In certain embodiments, distribution of the copies of the endogenous sequence will also be determined by use of known methods such as fluorescence staining. It is preferred that the endogenous sequence be present on more than one eukaryotic chromosome. In certain embodiments, depending on the desired level of yield of the gene of interest, the endogenous sequence will be selected on the basis of its copy number and genomic dispersion.

Particularly preferred endogenous sequences useful in the practice of this invention include transposon sequences (see e.g., Baltimore et al, Cell 40:481–482 (1985), sequences encoding members of the immunoglobulin gene superfamily, globin family sequences (including $\alpha,\beta,\gamma$ and $\delta$ globin sequences), retroviral sequences (including A, B, C, and D-type retrovirus sequences), retrovirus-like sequences (including IAP and C-type retrovirus-like sequences), histocompatibility sequences (sequences encoding elements of MHCI and II), and amplicon sequences (see, e.g., Windle et al., Genes and Development 5:150–174 (1991). Fragments of these endogenous sequences are also utilized in the practice of this invention. For example, amplicon sequences which have become partially dispersed through the host genome are particularly preferred. The target endogenous sequence may be functional or non-functional within the host cell. Selection of the endogenous sequences of this invention to avoid undesirable negative impact on cell growth or viability is routine in the art.

The immunoglobulin gene superfamily consists of molecules with immunoglobulin-like domains. Members of this family include class I and class II major histocompatibility antigens, immunoglobulins, T-cell receptor $\alpha,\beta,\gamma$ and $\delta$ chains, CD1, CD2, CD4, CD8, CD28, the $\gamma\delta$ and $\epsilon$ chains of CD3, OX-2, Thy-1, the intercellular or neural cell adhesion molecules (I-CAM or N-CAM), lymphocyte function associated antigen-3 (LFA-3), neurocytoplasmic protein (NCP-3), poly-Ig receptor, myelin-associated glycoprotein (MAG), high affinity IgE receptor, the major glycoprotein of peripheral myelin (Po), platelet derived growth factor receptor, colony stimulating factor-1 receptor, macrophage Fc receptor, Fc gamma receptors and carcinoembryonic antigen.

To obtain DNA encoding the endogenous sequence from sources other than a published source, if the DNA sequence from any source is known, one needs only to conduct hybridization screening with labelled DNA encoding the particle or fragments thereof (usually, greater than about 20, and ordinarily about 50 bp) in order to detect clones which contain homologous sequences in the cDNA libraries of the particular animal, followed by analyzing the clones by restriction enzyme analysis and nucleic acid sequencing to identify full-length clones. If full length clones are not present in the library, then appropriate fragments are recovered from the various clones and ligated at restriction sites common to the fragments to assemble a full-length clone. DNA encoding retrovirus-like particles from other animal species is obtained by probing libraries from such species with the hamster sequences, on by synthesizing the genes in vitro. DNA for other retrovirus-like particles having known sequence may be obtained with the use of analogous routine hybridization procedures.

The nucleic acid which is homologous to the endogenous nucleic acid sequences will be obtained by the methods described above.

Identification of the genomic DNA for the endogenous sequence is a straight-forward matter of probing a particular genomic library with the cDNA or its fragments which have been labelled with a detectable group, e.g. radiophosphorus, and recovering clone(s) containing the gene. The complete gene is pieced together by "walking" if necessary. Typically, such probes do not encode sequences with less than 60% homology to the endogenous sequence, and they range from about 10 to 100 bp in length.

Hybrid DNA technology may be employed for obtaining expression. The DNA sequence may be restriction mapped and appropriate sites for cleavage defined. In this way, the sequence may be excised and introduced into a vector having the appropriate control, transcription modulatory regions and regulatory signals. After obtaining expression, the gene product of interest may be recovered and subsequently purified.

In general, prokaryotes are used for cloning of DNA sequences in constructing the vectors useful in the invention. For example, E. coli K12 strain 294 (ATCC No. 31446) is particularly useful. Other microbial strains which may be used include E. coli B and E. coli X1776 (ATCC No. 31537). These examples are illustrative rather than limiting. Alternatively, in vitro methods of cloning, e.g. polymerase chain reaction, are suitable.

The gene products of this invention are expressed directly in recombinant cell culture as an N-terminal methionyl analogue, or as a fusion with a heterologous polypeptide, preferably a signal sequence or other polypeptide having a specific cleavage site at the N-terminus of the particle/portion. For example, in constructing a prokaryotic secretory expression vector for a gene product, the signal is employed with hosts that recognize that signal. When the secretory leader is "recognized" by the host, the host signal peptidase is capable of cleaving a fusion of the leader polypeptide fused at its C-terminus to the desired mature product. For host prokaryotes that do not process the native signal, the signal is substituted by a prokaryotic signal selected for example from the group of the alkaline phosphatase, penicillinase, Ipp or heat stable enterotoxin II leaders. For yeast secretion the native signal may be substituted by the yeast invertase, alpha factor or acid phosphatase leaders. In mammalian cell expression the native signal is satisfactory, although other mammalian secretory protein signals are suitable, as are viral secretory leaders, for example the herpes simplex gD signal.

The gene products of this invention may be expressed in any host cell, but preferably are synthesized in mammalian hosts. However, host cells from prokaryotes, fungi, yeast, insects and the like are also are used for expression. Exemplary prokaryotes are the strains suitable for cloning as well as E. coli W3110 (Fλ prototrophic, ATCC No. 27325), other enterobacteriaceae such as Serratia marescans, bacilli and various pseudomonads. Preferably the host cell should secrete minimal amounts of proteolytic enzymes.

Expression hosts typically are transformed with DNA encoding the hybrid which has been ligated into an expression vector. Such vectors ordinarily carry a replication site (although this is not necessary where chromosomal integration will occur). Expression vectors also include marker sequences which are capable of providing phenotypic selection in transformed cells, as will be discussed further below. For example, E. coli is typically transformed using pBR322, a plasmid derived from an E. coli species (Bolivar, et al. Gene 2:95[1977]). pBR322 contains genes for ampicillin and tetracycline resistance and thus provides easy means for identifying transformed cells, whether for purposes of cloning or expression. Expression vectors also optimally will contain sequences which are useful for the control of transcription and translation, e.g., promoters and Shine-Dalgarno sequences (for prokaryotes) or promoters and enhancers (for mammalian cells). The promoters may be, but need not be, inducible. While it is conceivable that expression vectors need not contain any expression control, replicative sequences or selection genes, their absence may hamper the identification of transformants and the achievement of high level particle expression.

Promoters suitable for use with prokaryotic hosts illustratively include the β-lactamase and lactose promoter systems (Chang et al., "Nature", 275:615 [1978]; and Goeddel et al., "Nature" 281:544 [1979]), alkaline phosphatase, the tryptophan (trp) promoter system (Goeddel "Nucleic Acids Res." 8:4057 [1980] and EPO Appln. Publ. No. 36,776) and hybrid promoters such as the tac promoter (H. de Boer et al., "Proc. Natl. Acad. Sci. USA" 80:2125-25 [1983]). However, other functional bacterial promoters are suitable. Their nucleotide sequences are generally known, thereby enabling a skilled worker operably to ligate them to DNA encoding the LHR (Siebenlist et al., "Cell" 20:269 [1980]) using linkers or adaptors to supply any required restriction sites. Promoters for use in bacterial systems also will contain a Shine-Dalgarno (S.D.) sequence operably linked to the DNA encoding the C-type retrovirus-like particle.

In addition to prokaryotes, eukaryotic microbes such as yeast or filamentous fungi are satisfactory. Saccharomyces cerevisiae is the most commonly used eukaryotic microorganism, although a number of other strains are commonly available. The plasmid YRp7 is a satisfactory expression vector in yeast (Stinchcomb, et al., Nature 282:39 [1979]; Kingsman et al, Gene 7:141 [1979]; Tschemper et al., Gene 10:157 [1980]). This plasmid already contains the trp1 gene which provides a selection marker for a mutant strain of yeast lacking the ability to grow in tryptophan, for example ATCC no. 44076 or PEP4-1 (Jones, Genetics 85:12 [1977]). The presence of the trp1 lesion as a characteristic of the yeast host cell genome then provides an effective environment for detecting transformation by growth in the absence of tryptophan.

Suitable promoting sequences for use with yeast hosts include the promoters for 3-phosphoglycerate kinase (Hitzeman et al., "J. Biol. Chem." 255:2073 [1980]) or other glycolytic enzymes (Hess et al., "J. Adv. Enzyme Reg." 7:149 [1968]; and Holland, "Biochemistry" 17:4900 [1978]), such as enolase, glyceraldehyde-3-phosphate dehydrogenase, hexokinase, pyruvate decarbozylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Patent Publication No. 73,657A.

Expression control sequences are known for sucaryotes. It is desirable that the gene of interest be under the control of transcription control elements, while the endogenous sequence introduced into the host cell with the gene of interest need not. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence which may be the signal for addition of the poly A tail to the 3' end of the coding sequence. All of these sequences are inserted into mammalian expression vectors.

Suitable promoters for controlling transcription from vectors in mammalian host cells are readily obtained from various sources, for example, the genomes of viruses such as polyoma virus, SV40, adenovirus, MMV (steroid inducible), retroviruses (e.g. the LTR of HIV), hepatitis-B virus and most preferably cytomegalovirus, or from heterologous mammalian promoters, e.g. the beta actin promoter. The early and late promoters of SV40 are conveniently obtained as an SV40 restriction fragment which also contains the SV40 viral origin of replication. Fiers et al., Nature, 273:113 (1978). The immediate early promoter of the human cytomegalovirus is conveniently obtained as a HindIII E restriction fragment. Greenaway, P. J. et al., Gene 18:355-360 (1982).

Transcription of a DNA encoding the genes of interest of this invention by higher eukaryotes is increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins, L. et al., PNAS 78:993 [1981]) and 3' Lusky, M. L., et al., Mol. Cell Bio. 3:1108 [1983]) as well as within the coding sequence itself (Osborne, T. F., et al., Mol. Cell Bio. 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant; animal, human or nucleated cells from other multicellular organisms) will also contain sequences necessary for the termination of transcription which may affect mRNA expression. These regions are transcribed as polyadenylated segments in the untranslated portion of the mRNA encoding the particle. The 3' untranslated regions also include transcription termination sites.

Expression vectors may contain a selection gene, also termed a selectable marker. Examples of suitable selectable markers for mammalian cells are dihydrofolate reductase (DHFR), thymidine kinase (TK) or neomycin. When such selectable markers are successfully transferred into a mammalian host cell, the transformed mammalian host cell is able to survive if placed under selective pressure. There are two widely used distinct categories of selective regimes. The first category is based on a cell's metabolism and the use of a mutant cell line which lacks the ability to grow independent of a supplemented media. Two examples are CHO DHFR cells and mouse LTK cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category of selective regimes is dominant selection which refers to a selection scheme used in any cell type and does not require the use of a mutant cell line. These schemes typically use a drug to arrest growth of a host cell. Those cells which are successfully transformed with a heterologous gene express a protein conferring drug resistance and thus survive the selection regimen. Examples of such dominant selection use the drugs neomycin (Southern et al., J. Molec. Appl. Genet. 1:327 (1982)), mycophenolic acid (Mulligan et al., Science 209:1422 (1980)) or hygromycin (Sugden et al., Mol. Cell. Biol. 5:410–413 (1985)). The three examples given above employ bacterial genes under eukaryotic control to convey resistance to the appropriate drug G418 or neomycin (genetic)n), xgpt (mycophenolic acid) or hygromycin, respectively.

Suitable eukaryotic host cells for expressing the genes utilized in this invention include monkey kidney CV1 line transformed by SV40 (COS-7, ATCC CRL 1651); human embryonic kidney line (293 or 293 cells subcloned for growth in suspension culture. Graham, F. L. et al., J. Gen Virol. 36:59 [1977]); baby hamster kidney cells (BHK, ATCC CCL 10); chinese hamster ovary-cells-DHFR (CHO, Urlaub and Chasin, PNAS (USA) 77:4216, [1980]); mouse sertoli cells (TM4, Mather, J. P., Biol. Reprod. 23:243–251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather, J. P. et al., Annals N.Y. Acad. Sci. 383:44–68 [1982]).

Construction of suitable vectors containing the desired coding and control sequences employ standard ligation techniques. Isolated plasmids or DNA fragments are cleaved, tailored, and religated in the form desired to form the plasmids required.

For analysis to confirm correct sequences in plasmids constructed, the ligation mixtures are used to transform E.

*coli* K12 strain 294 (ATCC 31446) and successful transformants selected by ampicillin or tetracycline resistance where appropriate. Plasmids from the transformants are prepared, analyzed by restriction and/or sequenced by the method of Messing et al., Nucleic Acids Res. 9:309 (1981) or by the method of Maxam et al., Methods in Enzymology 65:499 (1980).

Host cells are transformed with The expression vectors of this invention and cultured in conventional nutrient media modified as appropriate for inducing promoters, selecting transformants or amplifying the genes encoding the desired sequences. The host cells used to practice this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DME], Sigma) may be suitable for culturing the host cells. In addition, any of the media described in Ham and Wallace (*Meth. Enz.*, 58:44 [1979]), Barnes and Sato (*Anal. Biochem.*, 102:255 [1980]), U.S. Pat. No. 4,767,704, U.S. Pat. No. 4,657,866, WO 90/03430, WO 87/00195, U.S. Pat. No. Re. 30,985, U.S. Pat. No. 4,927,762, or U.S. Pat. No. 4,560,655 may be used as culture media for the host cells. Any of these media may be supplemented as necessary with hormones and/or other growth factors (such as insulin, transferrin, or epidermal growth factor), salts (such as sodium chloride, calcium, magnesium and phosphate), buffers (such as HEPES), nucleosides (such as adenosine and thymidine), antibiotics (such as Gentamycin), trace elements (defined as inorganic compounds usually present at final concentrations in the micromolar range), and glucose or an equivalent energy source. Any other necessary supplements may also be included at appropriate concentrations. The culture conditions, such as temperature, pH and the like, are those previously used with the host cell selected for expression, and will be apparent to the ordinarily skilled artisan.

The host cells referred to in this disclosure encompass cells in in vitro culture as well as cells which are within a host animal.

"Transformation" means introducing DNA into an organism so that the DNA is replicable, either as an extrachromosomal element or by chromosomal integration. Unless indicated otherwise, the method used herein for transformation of the host cells is the method of Graham, F. and van der Eb, A., Virology 52:456–457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen, F. N. et al., Proc. Natl. Acad. Sci. (USA), 69:2110 (1972).

"Transfection" refers to the introduction of DNA into a host cell whether or not any coding sequences are ultimately expressed. Numerous methods of transfection are known to the ordinarily skilled artisan, for example, CaPO$_4$ and electroporation. Transformation of the host cell is the indicium of successful transfection.

"PCR" (polymerase chain reaction) refers to a technique whereby a piece of DNA is amplified. Oligonucleotide primers which correspond to the 3' and 5' ends (sense or antisense strand-check) of the segment of the DNA to be amplified are hybridized under appropriate conditions and the enzyme Taq polymerase, or equivalent enzyme, is used to synthesize copies of the DNA located between the primer.

It is further envisioned the practice of this invention may involve recombinant production methods utilizing control elements introduced into cells already containing DNA encoding the desired product currently in use in the field. For example, a powerful promoter/enhancer element, a suppressor, or an exogenous transcription modulatory element, is inserted in the genome of the intended host cell in proximity and orientation sufficient to influence the transcription of DNA encoding the desired particle; the element does not encode the particle of this invention, but the DNA is present in the host cell genome. One next screens for cells making the desired product, or increased or decreased levels of expression, as desired.

The gene product is recovered and purified from recombinant cell cultures by known methods, including ammonium sulfate or ethanol precipitation, acid extraction, anion or cation exchange chromatography, phosphocellulose chromatography, immunoaffinity chromatography, hydroxyapatite chromatography and lectin chromatography.

Gene amplification and/or expression may be measured in a sample either directly, for example, by conventional Southern blotting or dot blot (DNA analysis) using an appropriately labelled probe, based on the sequences provided herein. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured either by Northern blotting to quantitate the transcription of mRNA (Thomas (1980) Proc. Natl. Acad. Sci. USA 77:5201–5205), dot blots, and in situ hybridization, or by immunological methods, such as immunohistochemical staining of tissue sections and assay of cell culture or body fluids, to directly quantitate the expression of gene product. With immunohistochemical staining techniques, a cell sample is prepared, typically by dehydration and fixation, followed by reaction with labeled antibodies specific for the gene product, where the labels are usually visually detectable, such as enzymatic labels, fluorescent labels, luminescent labels, and the like. A particularly sensitive staining technique suitable for use in the present invention is described by Hsu et al. (1980) Am. J. Clin. Path. 75:734–738.

Antibodies useful for immunohistochemical staining and/or assay of sample fluids may be either monoclonal or polyclonal. Conveniently, the antibodies may be prepared against a synthetic peptide based on the DNA sequences of the gene of interest. Such synthetic peptides may then be used as an immunogen in preparing antibodies by wellknown techniques. Alternatively, the natural gene product and/or portions thereof may be isolated and used as the immunogen.

While CHO cell lines are particularly appropriate for the application of these methods, these methods are used routinely with any host cell described above.

Cell lines are evaluated for expression of endogenous sequences and for expression of the gene of interest. Detection of expression may be made by immunoassay for structural proteins, enzymatic assay for reverse transcriptase activity, blot analysis for RNA transcripts, and electron microscope examination of cell sections for the presence of gene products.

In other embodiments, high expressor subclones are isolated through routine screening as described above. For example, subclones of parental cells are evaluated for expression of RNA sequences by blot analysis using probes consisting of fragments of the nucleic acid sequences of the gene of interest. Different transfected cell lines may vary significantly in their level of gene expression and it is anticipated that variation will occur in non-transfected subclones as well.

This invention also contemplates alternate selection schemes. Many direct selection schemes employing antibodies directed to the gene products can be employed. One embodiment involves incubation of a host cell in the presence of protein antibodies and complement. The antibody and complement lyse expressor cell lines and leave only non-expressor cells as survivors. Some routine experimentation with antibody concentrations may be necessary in order to select for high expressor cells in the event that non-expressor cells do not exist in the initial population.

A second approach using the fluorescence activated cell sorter (FACS) allows flexibility in the selection of high and low-expressor cells. Host cells are stained using anti-gene product primary antibody and a fluorescein conjugated second antibody. High expressor cells show high fluorescence and low expressors low fluorescence. Physical sorting of individual cells by FACS according to fluorescence intensity is used to enrich for a population of cells which express high levels of the gene of interest. Multiple rounds of FACS sorting enhances the selection procedure. Once a population of high-expressing cells is obtained, subclones are propagated and analyzed more rigorously for gene expression as outlined for the screening protocol above.

The nucleic acid sequences encoding the endogenous sequences and the genes of interest of this invention are desirably incorporated into a host cell in more than one copy. Nucleic acid homologous to the endogenous nucleic acid is introduced at levels of approximately 5 to 10 μg DNA/cell and found to yield desirable result. For those embodiments desiring improved expression levels, this amount of nucleic acid may be boosted, for example by 10 or 20 times the above amount, or by any amount sufficient to yield the desired result.

This invention also encompasses the introduction of nucleic acid into a cell or tissue of an animal either in vitro, in vivo or ex vivo. In some instances, the nucleic acid is intended to replace (or act in place of) a functionally deficient endogenous gene, to confer on the host the ability to produce a therapeutic polypeptide, to cause repression of an undesirable gene product, or to stimulate an immune response. Methods for introducing nucleic acid into such cells or tissues include methods for in vitro introduction of nucleic acid discussed above, including the insertion of naked DNA or RNA (such as by injection of the nucleic acid into a tissue), the reintroduction into a tissue of a cell modified ex vivo to transcribe and express heterologous nucleic acid, the provision of nucleic acid in liposomes or other carrier, the use of a vector such as a virus, retrovirus, phage, plasmid etc., or techniques such as electroporation. Methods of electroporation in vitro are disclosed in Barsoum, *DNA and Cell Biology*, 9 (4):293–300 (1990). Electroporation may be used in vivo or ex vivo, for example by injecting the desired nucleic acid into a tissue and then applying current-by electrodes or other suitable equipment-to the target tissue. Other known methods for the introduction of nucleic acid into cells or tissues are suitable for the practice of this invention.

Transgenic animals which transcribe and express heterologous nucleic acid are encompassed by this invention. Such animals have been produced by transfecting germ cells, somatic cells, or embryos with heterologous nucleic acid according to the methods of this invention, using endogenous sequences for homologous recombination and introduction of heterologous sequences. The modified cells/embryos are suitably implanted and allowed to mature into or stably integrate into adult animals containing the heterologous DNA. A reproducible percentage of such animals transcribe and express the heterologous nucleic acid as protein which can be identified in tissues including blood or serum. Methods for making transgenic animals are described in U.S. Pat. No. 4,396,601.

The formulation and mode of administration for in vitro use will be determined by the experimental criteria as described above. Aqueous formulations that are compatible with the culture or perfusion medium will normally be used.

Nucleic acid for introduction to tissues or cells in vivo or ex vivo, and modified cells/tissue for parenteral administration may be formulated in a unit dosage injectable form (solution, suspension, emulsion) in association with a pharmaceutically acceptable parenteral carrier. Such carriers are inherently nontoxic, and non-therapeutic. Examples of such carriers are water, saline, Ringer's solution, dextrose solution, and 5% human serum albumin. Nonaqueous carriers such as fixed oils and ethyl oleate can also be used. Liposomes may be used as carriers. The carrier may contain minor amounts of additives such as substances that enhance isotonicity and chemical stability, e.g., buffers and preservatives.

The cells or tissues of this invention used in therapy are formulated and dosages established in a fashion consistent with good medical practice taking into account the disorder to be treated, the condition of the individual patient, the site of delivery of the cell or tissue, the method of administration and other factors known to practitioners. The cells or tissues are prepared for administration as described above.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below, but should not be construed to limit the invention.

EXAMPLE

The following materials and methods information applies to all examples below.

*Cells and cell culture.* DHFR minus Chinese hamster ovary cells, originally established by Urlaub and Chasin, PNAS 77:4216–4220 (1980), were grown in standard DMEM/Ham F12 (Gibco) based cell culture medium which was modified with respect to the composition and concentration of a number of amino acids. This medium contains the components glycine, hypoxanthine and thymidine in order to overcome the DHFR deficiency of these cells ("alpha modified medium").

One or two days prior to transfection, cells were trypsinized and seeded into 60 mm plates at a density allowing for about 50%–70% confluency on the day of transfection.

The transfections were performed with 5 µg of CsCl2-purified plasmid DNA (total), with two or three plasmids mixed together at defined molar ratios, as specified in the particular example, one of which contained the DHFR expression cassette. The procedure used was a modification of the method described by Graham and van der Eb, *Virology* 52:456 (1973). Briefly, cells were transfected by addition of the calcium phosphate DNA precipitate. The precipitate was left for 4 hours on the cells. Then, medium was exchanged with fresh, non-selective medium and incubated at 37° C. After 48 hours cells were trypsinized and distributed into 100 mm plates in selective medium containing dialyzed fetal bovine serum and lacking the components glycine, hypoxanthine and thymidine. In some experiments methotrexate (MTX) was added to the medium at concentrations ranging from 30 nM to 1000 nM, as indicated. Cells were incubated at 37° C. for the following 2 to 4 weeks and the medium replaced every other 3 to 4 days until colonies arose.

Analysis of transfections and evaluation of expression levels for the desired genes. Some transfections were analyzed after 2 to 4 weeks in selective medium by counting the number of colonies per plate. This was done by washing the plates with water and then adding 2 ml per plate of a PBS/Ethanol (1:1) solution containing 2% Methylene blue. The dye was decanted after 2 minutes and residual dye washed off with water. The number of colonies per plate was counted using a video connected plate reader (Artek).

Expression levels of individual cell clones were analyzed after expansion of the individual clones to cell lines in 6 well plates. The cell culture supernatant was assayed after exposure to fresh serum-free medium for 6 days (approximately $8 \times 10^5$ c/well). Enzyme linked immunoassays were used to evaluate the expression of the secreted proteins of interest in these examples, recombinant tissue plasminogen activator (rtPA), and a hybrid antibody (CD4IgG).

Endogenous, Retrovirus-like DNA sequences from CHO cell. The retroviral sequences used in the transfections are members of two different types of sequence families in the CHO genome. One of the sequences is related to the Syrian hamster IAP sequences–referred to herein as IAP sequence family I. This sequence has been isolated from the CHO-genome as a genomic DNA fragment (EcoRI-Sal I) of 2.9 kb of length. Also, a 0.4 kb subfragment from this DNA was used. The 0.4 kb fragment (Aha II-Pst I) represents part of the 5'LTR sequence of the larger 2.9 kb "full length" IAP-like DNA. The 2.9 kb "full length" IAP DNA spans from an EcoRI site about 400 basepairs upstream of the 5' LTR to a Sal I site inside of the 3' LTR. This retrovirus-like DNA has an internal 4.5 kb deletion which excises a major part of the "virus genome" (FIG. 1-1). The copy number of this family of sequences has been estimated to be in the range from 100 to 300 per haploid genome, Anderson et al., *J. Virology* 64:2021-2032 (1990).

Figures 1, 2:
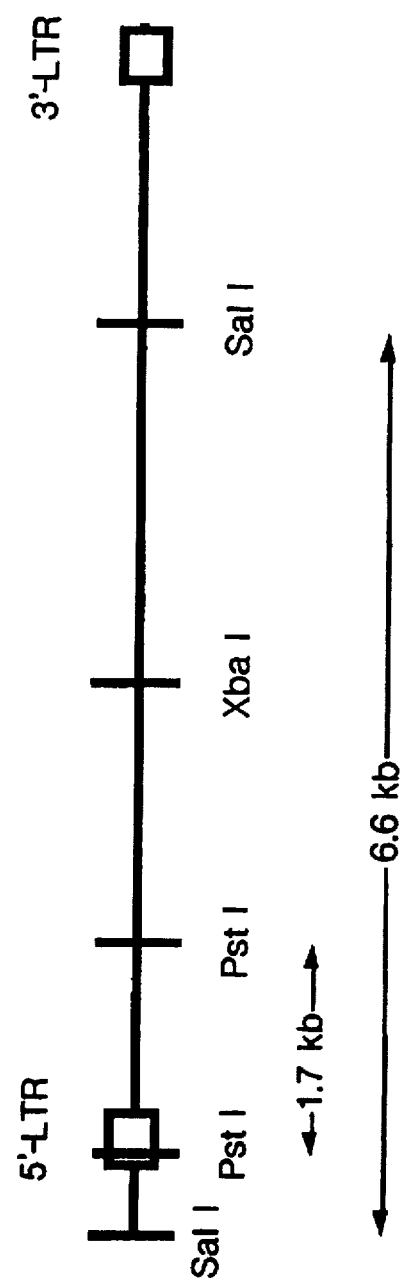
Figure 2:
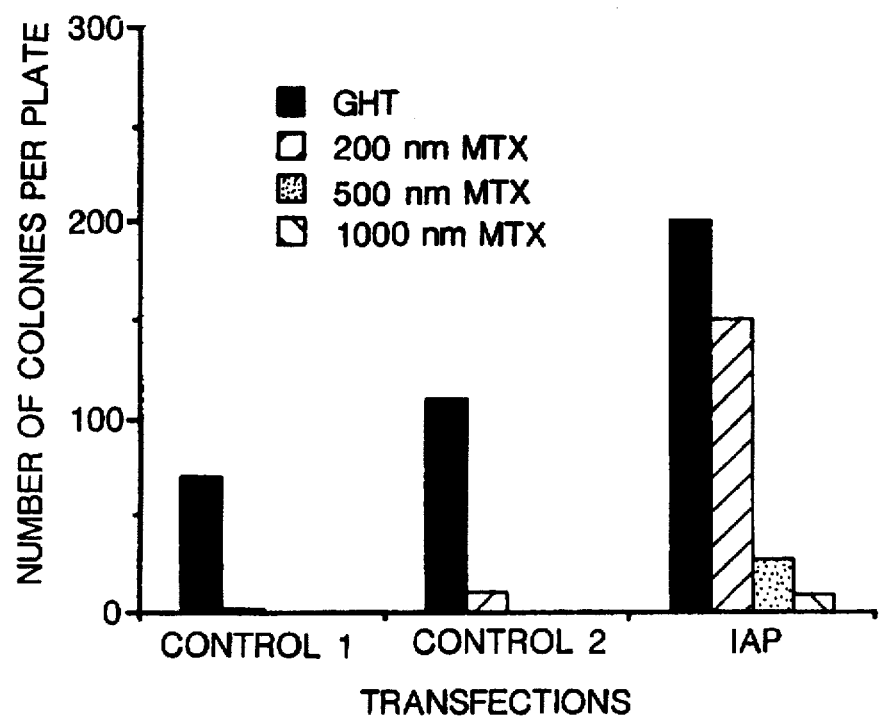

The second type of retrovirus-like sequences isolated from the CHO genome belongs to a family of sequences with homologies to mammalian C-type viruses, Anderson et al., *Virology* 181:305-311 (1991). From this family of sequences a 6.6 kb fragment representing about 70% of a complete retrovirus genome 450 basepairs upstream of the 5' LTR to a Sal 1 site 2 kb upstream of the 3' LTR was used. Also, an internal 1.7 kb PstI-PstI fragment including the 5' LTR was used in transfections (FIG. 1-2). The abundance of this family of sequences in the CHO-genome has been estimated to be about 100-300 copies per haploid genome as well.

The IAP- and C-type sequences were inserted into pUC-based vectors for co-transfection or incorporated into the DHFR-expression vector.

EXAMPLE 1

Increase transfection efficiency in co-transfections with DHFR plasmid and plasmids containing IAP-like retrovirus DNA from CHO cells. Three co-transfections were performed in parallel:

a) the control transfection was done with a 1:9 ratio between the DHFR expression vector and an expression vector for CD4IgG.

b) another control transfection was done with a 1:1:8 ratio between the same DHFR expression vector, the CD4IgG-expression vector and a PUC vector containing a 2.9 kb c) the third transfection was performed with a 1:1:8 molar ratio between the DHFR expression vector, the CD4IgG-expression vector and the PUC vector containing a 2.9 kb insert of IAP-retrovirus like sequence.

First, one set of plates was selected in GHT minus medium for about 2 weeks until viable and healthy colonies were visible. The colonies were stained as described above and counted. A second, third and fourth set of plates was selected in GHT minus medium which contained MTX at concentrations of 100 nM, 300 nM and 1000 nM. The result is given in FIG. 2, which shows the number of selected colonies in co-transfections containing and lacking IAP-retroviral sequences In comparison to the two control transfections a) and b), the transfection containing the retroviral DNA resulted in the largest number of colonies both upon selection in GHT-minus medium as well as in medium which was supplemented with MTX. In this part of the experiment the effect of the retroviral sequence was most evident: At 200, 500 and 1000 nm MTX respectively, 150, 26 and 9 colonies survived the selection procedure, whereas in the control-1 cases only 2 colonies grew in 200 nM MTX and none at higher concentrations. In the control-2 experiment, 10 colonies grew at 200 nm MTX and again none at higher concentrations. The slightly larger number of colonies upon GHT selection in the control-2 case compared to the control-1 case can be explained by the use of a large excess of CD4IgG expression vector (10 fold) in this instance. In control-2 there was only a 1:1 ratio between DHFR expression vector and CD4IgG vector. Thus a contraselective force by high expression levels of the co-transfected CD4IgG DNA may have influenced the outcome of the experiment.

Overall, the efficiency of transfection was found to be greatly enhanced when the 2.9 kb fragment of the IAP-like sequence was co-transfected together with the DHFR selection plasmid. This is most evident in those most stringent cases where selection was applied through the addition of MTX to the cell culture medium. Only clones expressing rather high levels of the DHFR enzyme would be able to overcome this selection step.

EXAMPLE 2

Increase transfection efficiency in co-transfections with DHFR expression vector and plasmids containing C-type retroviral DNA from CHO cells.

In this example, the DHFR containing plasmid was co-transfected into CHO cells together with a plasmid containing or lacking C-type retroviral sequences. Two C-type retroviral sequences were compared: a 6.6 kb genomic fragment of a proviral clone containing the 5' LTR sequence and about 60% of a "complete C-type" genome, or a 1.7 kb sub-cloned fragment which is lacking the distal portion of the 5' LTR and covers only about 20% of a complete C-type genome. Both sequences had been inserted into pUC215. The pUC215 vector (minus retroviral sequences) was used for the control transfection.

Figure 3:
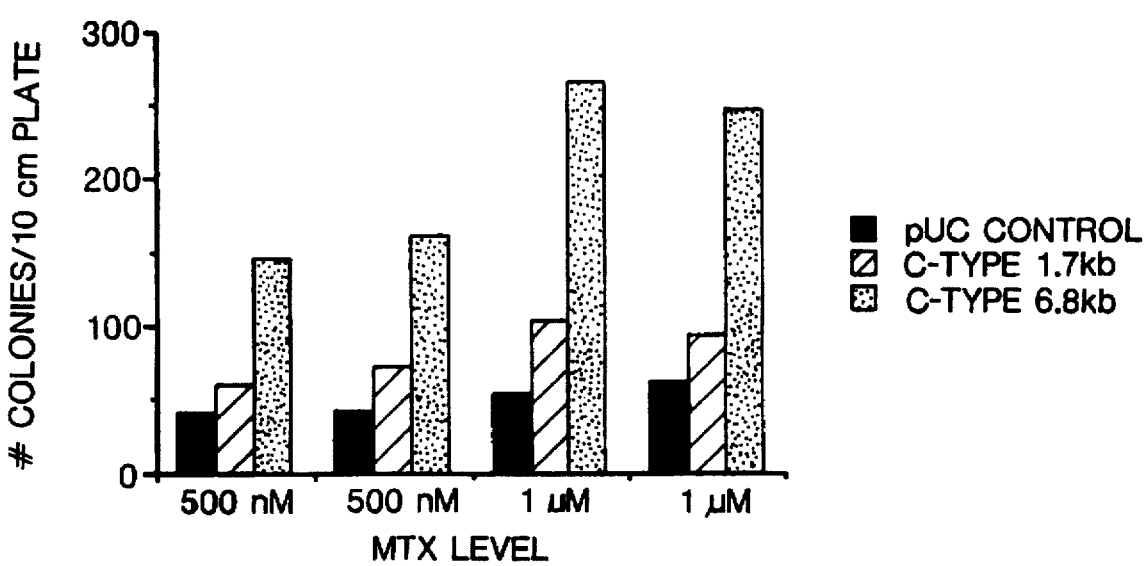
FIG. 3. Number of MTX resistant clones generated by co-transfection of the DHFR plasmid with a pUC control vector or C-type retroviral sequences.

The influence of C-type retroviral sequences on transfection frequencies was measured in two ways. Initially, colonies which appeared following selection on GHT minus media were counted. This represented the overall transfection frequencies. No difference was discerned between the C-type containing vectors or the control, pUC215 vector. However, when the GHT minus plates of colonies were pooled and subjected to selection at 500 nM and 1 mM MTX, significantly more colonies per 10 cm plate were generated when the vectors contained the 6.8 kb or 1.7 kb retroviral fragments (FIG. 3). The 6.8 kb retroviral sequence generated 3.6 times more colonies at 500 nM MTX than the control, and produced 4.4 times more colonies at the 1 mM MTX level. Likewise, the shorter retroviral sequence resulted in a moderate increase of 1.6 and 1.7 times more colonies than the control at the two MTX levels.

EXAMPLE 3

Expression levels of randomly selected cell clones resulting from transfections containing a 2.9 kb, but not a 0.4 kb IAP retrovirus-like DNA are better as compared to control transfection.

Three types of DHFR expression vectors were used in this experiment:

a) a regular DHFR expression vector (control)

b) a DHFR expression vector which contained a 2.9 kb long insert of IAP sequence, representing an almost full length retrovirus genome with 2 LTRs but lacking a large region within the "virus genome".

c) a DHFR expression vector which contained a 0.4 kb fragment derived from the same IAP sequence, representing only a part of the left end of the "virus genome".

These DHFR expression vectors were co-transfected at a 1:10 molar ratio with an expression vector for CD4IgG. Randomly chosen colonies were cloned, expanded to individual cell lines and assayed for their expression of CD4IgG using a CD4IgG ELISA.

Figures 1, 4:
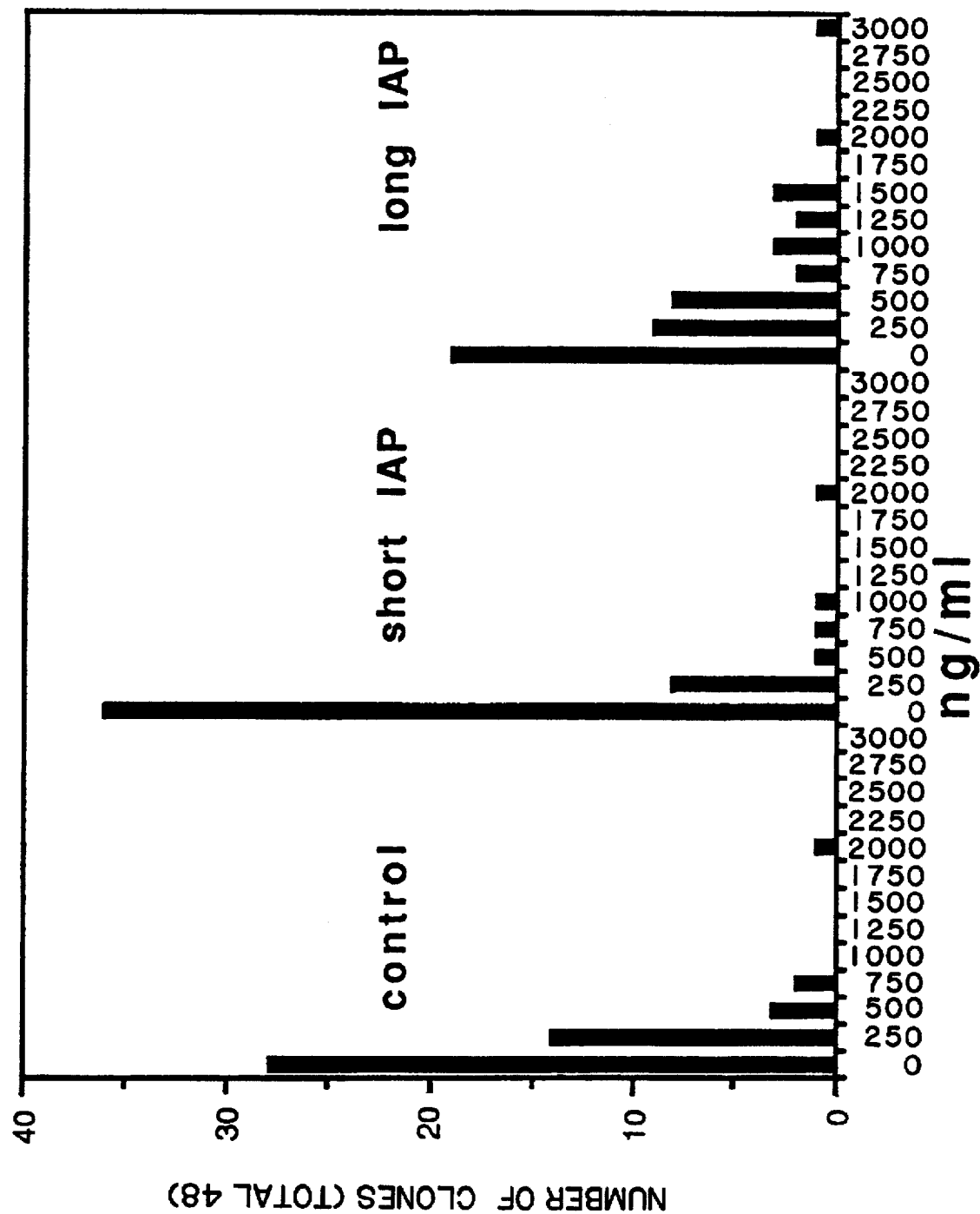
Figures 2, 4:
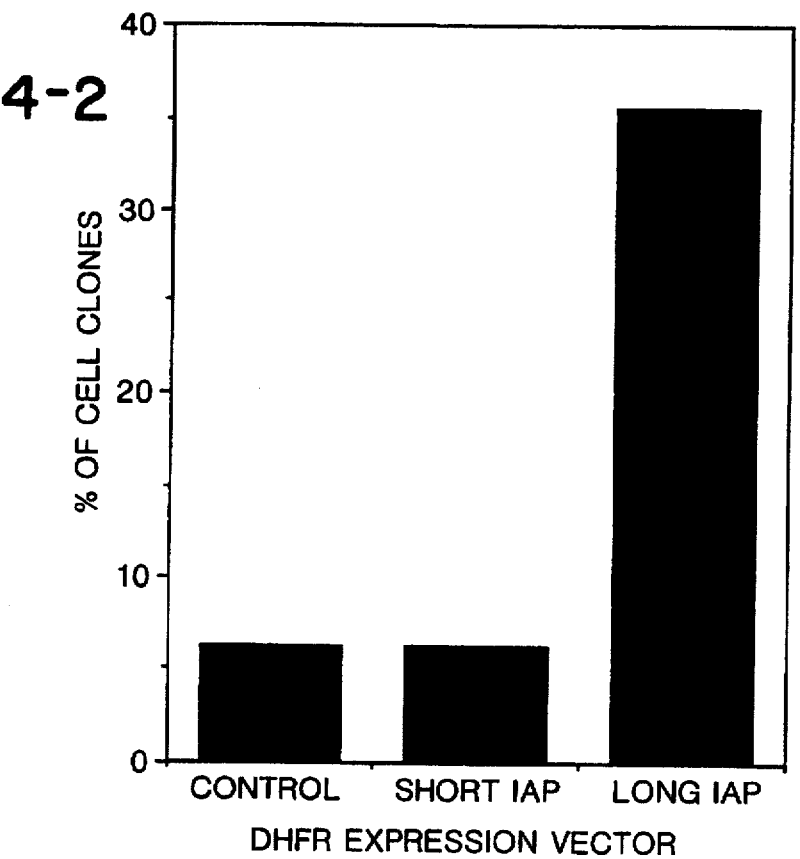
Figures 3, 4:
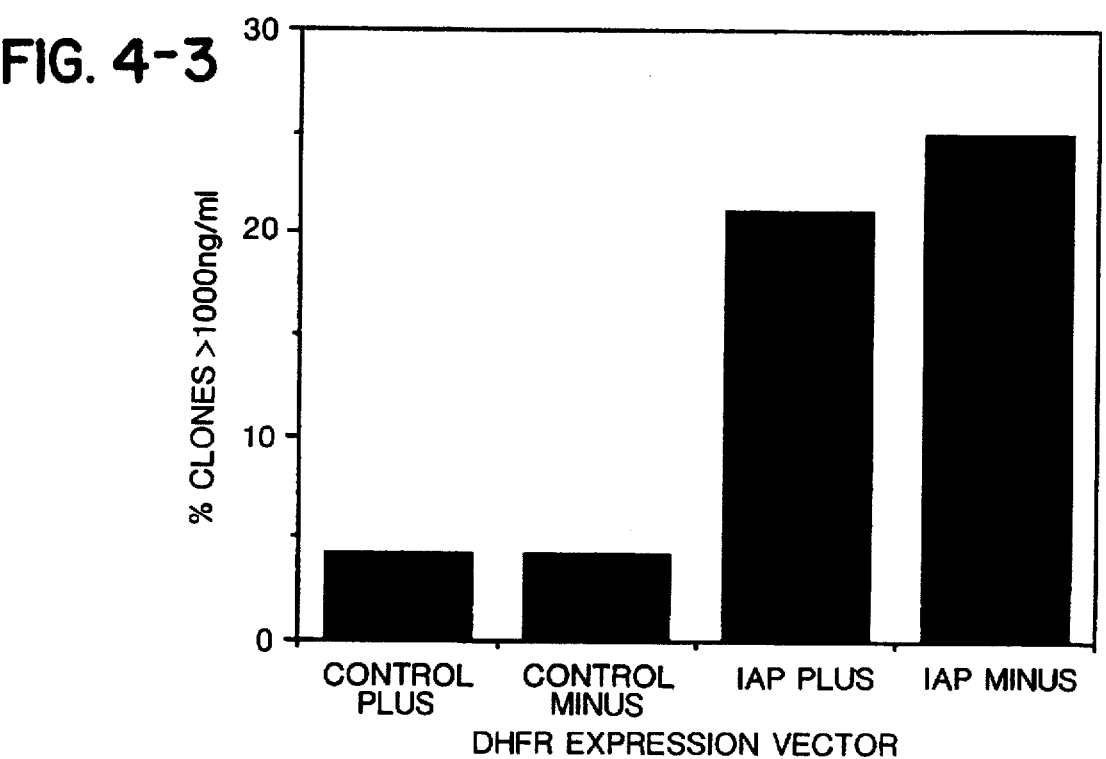
Figure 4:
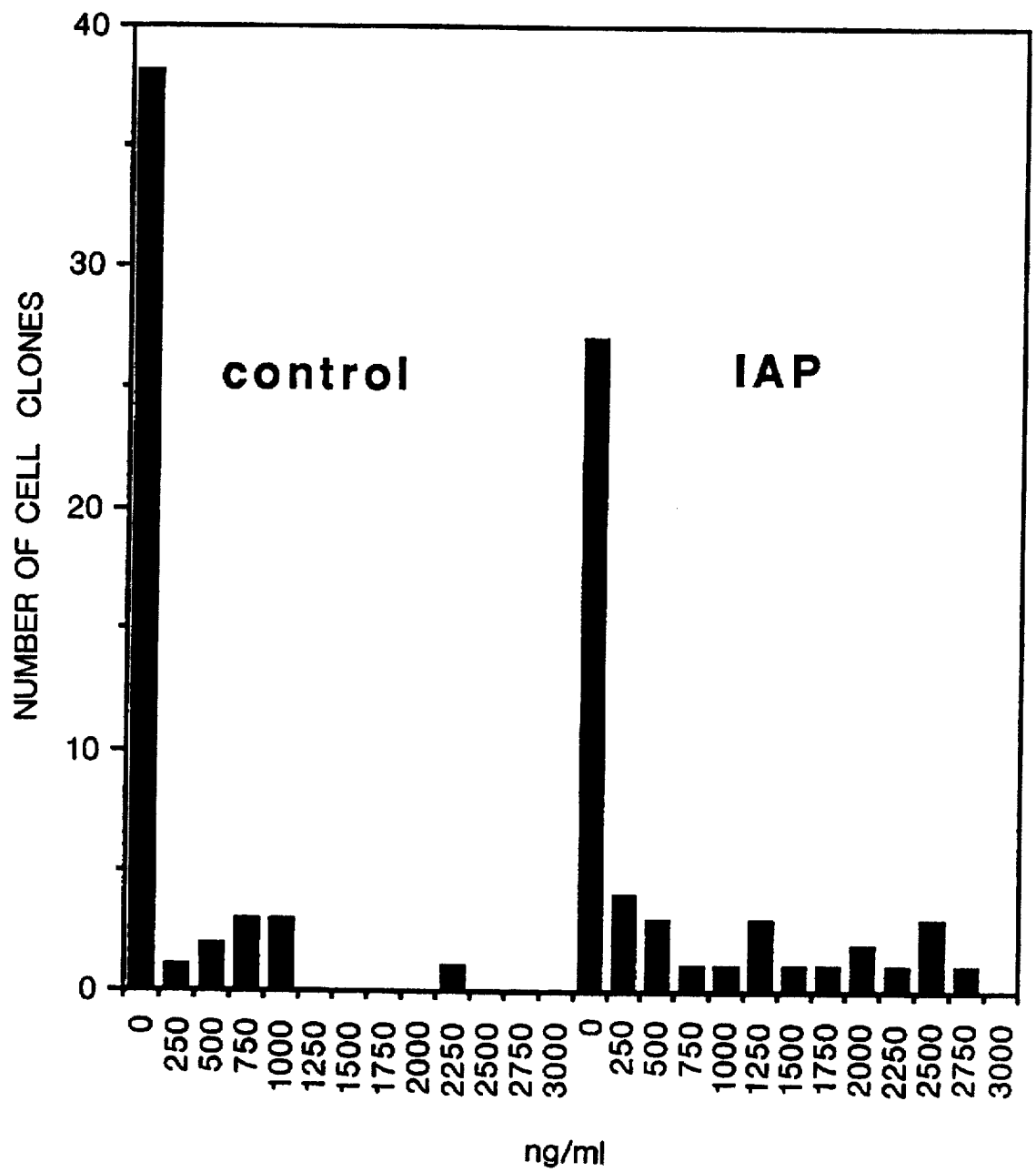

The selection procedure after transfection was done with GHT minus medium only. In two separate experiments 48 colonies (24 in each experiment) were cloned and expanded to individual cell lines for each case. Because there were no significant differences in the results obtained when analyzing the same type of transfection of the two experiments the data were evaluated together (FIG. 4-1 ). In both experiments, the case using the 2.9 kb long retroviral sequence (b) resulted in a much higher frequency of cell clones expressing the secondary gene of interest (CD4IgG at high levels. The number of cell clones expressing less than 250 ng/ml was lowest in the transfection with the long IAP retrovirus DNA insert. A larger percentage of clones in the long IAP insert group showed good expression of CD4IgG. The result also indicate that there was no difference in the expression levels when a short IAP DNA sequence was inserted into the DHFR expression vector (FIG. 4-1).

In FIG. 4-2 is shown the percentage of cell clones which express at the acceptable expression level of greater than 500 ng/ml. It is evident that in the case of the large IAP insert a much higher frequency of good expressors were found.

In another experiment of this type the effect of the orientation of the 2.9 kb retroviral DNA insert in The DHFR expression vector was evaluated. For that reason three transfections were performed as before. Four types of DHFR expression vectors were used in this experiment:

a) a regular DHFR expression vector (control plus) (for plus orientation inserts).

b) a regular DHFR expression vector (control minus) (for minus orientation inserts). The difference between the two control DHFR plasmids is the orientation of a short multiple cloning site of 35 base pairs.

c) a DHFR expression vector which contained the 2.9 kb long insert of IAP sequence in the "plus" orientation.

d) a DHFR expression vector which contained the 2.9 kb long insert of IAP sequence in the "minus" orientation.

These DHFR expression vectors were co-transfected at a 1:10 molar ratio with an expression vector for CD4IgG. 24 randomly chosen colonies were cloned for each case, expanded to individual cell lines and assayed for their expression of CD4IgG using a CD4IgG ELISA. The percent of cell lines expressing CD4IgG at levels higher than 1000 ng/ml are given in FIG. 4-3.

It is evident from this data that the orientation of the IAP-sequence does not play a role in the achieved expression levels in randomly selected clones. In the following graph the individually achieved titer ranges are given for all the clones analyzed. The data for the two orientations of the control DHFR plasmids and the DHFR-IAP plasmids have been combined and are presented together in FIG. 4-4.

EXAMPLE 4

Increased expression levels for rTPA (recombinant tissue plasminogen activator) of randomly chosen cell clones resulting from co-transfections with a DHFR expression plasmid containing a 2.9 kb fragment of IAP like retrovirus like DNA from CHO cells.

The influence of the IAP sequences on co-transfection with a rtPA gene was measured. Two DHFR expression plasmids were used. One of them contained the 2.9 kb IAP retrovirus like DNA (IAP-DHFR), the other lacked it (Control-DHFR). A separate rtPA expression vector was co-transfected. The rtPA expression plasmid was included in the co-transfection mixture at a 10 fold molar excess. The number of MTX resistant clones as well as the level of rtPA gene expression was evaluated.

Following the initial GHT minus selection there were approximately 50% more colonies on the IAP-DHFR plates than the control DHFR plates. This indicates a higher transfection frequency for the plasmid containing retroviral sequences. The rtPA titer from these initial plates was measured when the plates became confluent. The IAP-DHFR population of cells produced 15% more rtPA than the control cells on GHT minus selective media, however there was a 720% increase in rtPA production by an IAP-DHFR population of cells selected in medium containing 30 nM MTX.

Figure 5:
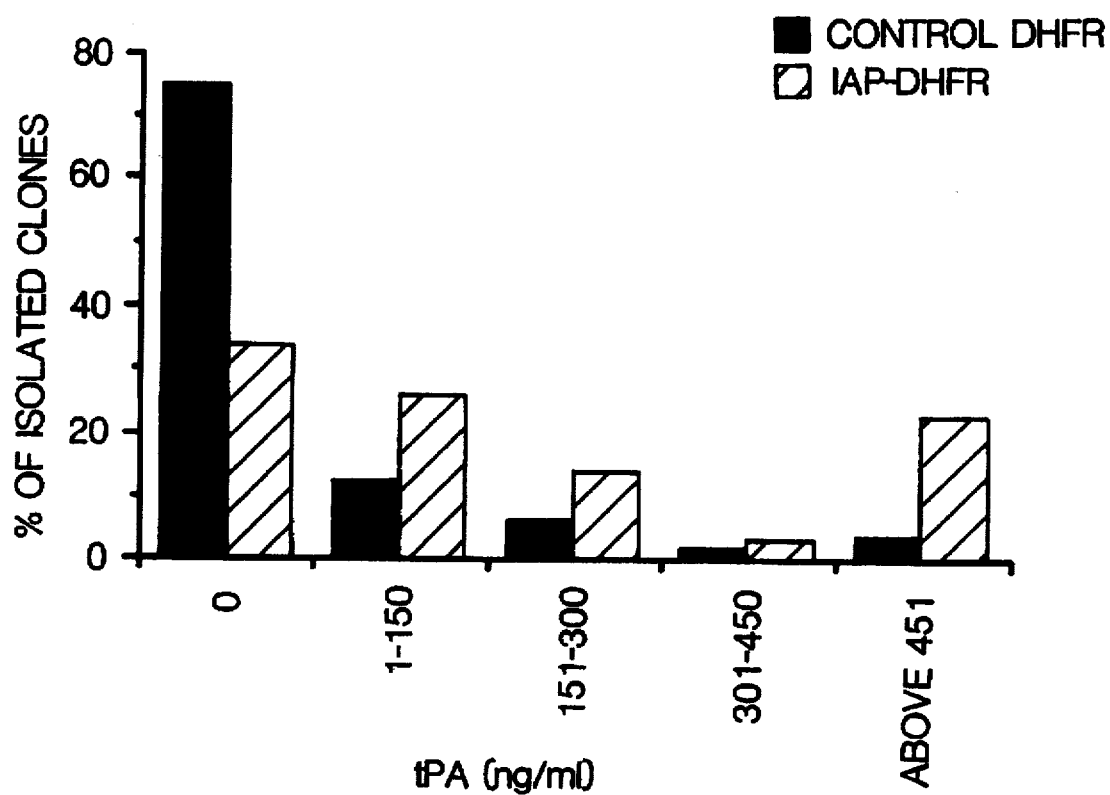
FIG. 5: Analysis of rtPA expression in isolated clones selected at 30 nM MTX.

Individual, random clones were isolated from the 30 nM MTX plates from the IAP-DHFR and control transfections and assayed for rtPA production. The expression profiles are shown in FIG. 5. 36 of the 48 clones (75%) from the control transfection did not express detectable rtPA levels, whereas only 12 of the 35 clones (34%) from the IAP-DHFR transfection were below detection levels. The rtPA expression level of 450 ng/ml and above was significantly better for the clones from The IAP-DHFR transfection, 23%, compared to only 4% for the control situation.

I claim:

1. A method for obtaining animal cells having increased expression of a heterologous gene comprising:

a. obtaining an animal cell having a first endogenous nucleic acid sequence which is present in at least 50 copies and dispersed within the genome of the host cell and is present in transcriptionally active areas of the genome; and b. introducing into the cell a second nucleic acid sequence homologous to the endogenous sequence and a third nucleic acid sequence which encodes a heterologous gene.

2. The method of claim 1 wherein the endogenous sequence is a retrovirus-like sequence.

3. The method of claim 2 wherein the endogenous retrovirus-like sequence is unable to form infectious virus.

4. The method of claim 1 wherein the third nucleic acid sequence is under the control of sequences which promote transcription and translation.

5. The method of claim 1, wherein the cell is a Chinese hamster ovary cell.

6. The method of claim 1, wherein the cell is a Chinese hamster ovary cell and the endogenous nucleic acid sequence is selected from the group consisting of IAP-retroviral sequences, type C retroviral sequences, and sequences which are homologous thereto but do not encode IAP particles or type C retroviruses.

7. The method of claim 6 wherein the first endogenous nucleic acid sequence is an IAP-retroviral sequence.

8. The method of claim 6 wherein the first endogenous nucleic acid sequence is a type C retroviral sequence.

9. The method of claim 1, wherein said third nucleic acid sequence is introduced into said cell in greater copy number than is said second nucleic acid sequence.

10. The method of claim 1, wherein the first endogenous nucleic acid sequence is present in more than 100 copies in the genome of the cell.

11. The method of claim 1, wherein said first nucleic acid sequence is located on at least two different chromosomes of the cell.

12. The method of claim 1, wherein said second nucleic acid sequence is introduced into said cell as a single strand.

13. A method for obtaining animal cells having increased expression of a heterologous gene comprising:

a. identifying a first nucleic acid sequence which is endogenous in an animal cell and which is present in at least 50 copies dispersed through the genome of the cell and is present in transcriptionally active areas of the genome; and b. introducing into the cell a second nucleic acid sequence homologous to the first nucleic acid sequence and a third nucleic acid sequence which encodes a heterologous gene.

14. A method for obtaining animal cells having increased expression of a heterologous gene comprising:

a. obtaining an animal cell having a first endogenous nucleic acid sequence which is present in at least 50 copies in the animal cell genome, the copies being present in transcriptionally active regions of the genome, wherein any two copies are separated from each other by being located on different chromosomes or located at least 100,000 base pairs apart on the same chromosome; and b. introducing into the cell a second nucleic acid sequence homologous to the endogenous sequence and a third nucleic acid sequence which encodes a heterologous gene.

* * * * *